(12) United States Patent
Perry

(10) Patent No.: US 7,732,614 B2
(45) Date of Patent: Jun. 8, 2010

(54) 2,6-QUINOLINYL DERIVATIVES, PROCESSES FOR PREPARING THEM AND THEIR USES

(75) Inventor: Benjamin Perry, Cambridge (GB)

(73) Assignee: UCB S.A., Brussels (BE)

( * ) Notice: Subject to any disclaimer, the term of this patent is extended or adjusted under 35 U.S.C. 154(b) by 1034 days.

(21) Appl. No.: 11/450,694

(22) Filed: Jun. 9, 2006

(65) Prior Publication Data
US 2007/0004775 A1    Jan. 4, 2007

Related U.S. Application Data

(63) Continuation-in-part of application No. 11/206,158, filed on Aug. 18, 2005, now abandoned.

(30) Foreign Application Priority Data

Jun. 9, 2005  (GB) ................................. 0511781.7
Jan. 6, 2006  (GB) ................................. 0600213.3

(51) Int. Cl.
C07D 215/38    (2006.01)
(52) U.S. Cl. ...................... 546/173; 514/314
(58) Field of Classification Search ................. 546/173; 514/314
See application file for complete search history.

(56) References Cited

U.S. PATENT DOCUMENTS

2005/0020626 A1    1/2005  Mathias

FOREIGN PATENT DOCUMENTS

| EP | 0 798 291 | 10/1997 |
|---|---|---|
| WO | WO 99/10312 | 3/1999 |
| WO | WO 00/15612 | 3/2000 |
| WO | WO 00/66572 | 11/2000 |
| WO | WO 02/18320 | 3/2002 |
| WO | WO 03/072536 | 9/2003 |
| WO | WO 03/093237 | 11/2003 |
| WO | WO 2005/061440 | 7/2005 |
| WO | 2006131200 | * 12/2006 |
| WO | WO 2006/131200 | 12/2006 |

OTHER PUBLICATIONS

Porter, J.R. et al. *Discovery and Evaluation of N-(triazin-1,3,5-yl) Phenylalanine Derivatives as VLA-4 Integrin Antagonists*, Bioorg. Med. Chem. Lett., 2002, pp. 1591-1594, No. 12.
Makoto, M. *New Alanine Derivative*, Patent Abstracts of Japan, 1997, Pub. No. 09087291, Application No. 07270665.
Mar. 31, 2005 STN International search results.
CAS Abstract Reg. No. 623146-78-1, Dec. 2003.
Vela, M. et al. *Syntheses of 1- and 2-Naphthol Analogues of DL-Tyrosine. Potential Fluorescent Probes of Peptide Structure and Dynamics in Complex Environments*, J. Org. Chem., 1990, vol. 55, No. 9, pp. 2913-2918.

* cited by examiner

*Primary Examiner*—D. Margaret Seaman
(74) *Attorney, Agent, or Firm*—Hoxie & Associates LLC

(57) ABSTRACT

The present invention concerns 2,6-quinolinyl derivatives, processes for preparing them, pharmaceutical compositions containing them and their use as pharmaceuticals.

8 Claims, No Drawings

2,6-QUINOLINYL DERIVATIVES, PROCESSES FOR PREPARING THEM AND THEIR USES

This application is a Continuation-in-Part of U.S. Ser. No. 11/206,158 filed Aug. 18, 2005 now abandoned and claims priority to British Patent Application No. 0600213.3 filed Jan. 6, 2006 and British Patent Application No. 0511781.7 filed Jun. 9, 2005, the contents of which applications are incorporated herein by reference.

The present invention concerns 2,6-quinolinyl derivatives, processes for preparing them, pharmaceutical compositions containing them and their use as pharmaceuticals.

The integrin α4β1 (also termed VLA-4 or Very Late Antigen-4 and designated CD49d/CD29) is predominantly expressed on eosinophils, lymphocytes, monocytes and basophils. It binds primarily to the vascular cell surface adhesion molecule VCAM-1 that is expressed on endothelium in response to inflammatory cytokines (TNF-α, IL-1 and selectively IL-4 and IL-13) and to the extracellular matrix protein fibronectin.

Because α4β1 is not expressed on circulating neutrophils, which are the first defense against infection, it is a target for the pharmacological control of inflammatory diseases.

Several in vitro and in vivo studies have indicated an important role of α4β1 in cell adhesion mediated inflammatory pathologies and that blocking its function is beneficial. Diseases include asthma, multiple sclerosis (MS), rheumatoid arthritis (RA) or inflammatory bowel diseases.

α4β1 is also expressed on leukemic cells that show increased survival through binding to fibronectin expressed on bone marrow stromal cells. Blocking this interaction in the presence of chemotherapy is beneficial in preventing relapse of acute myelogenous leukemia.

α4β1 and VCAM-1 have also been identified in smooth muscle cells from intimal atherosclerotic thickening of adult aorta. Blocking this interaction is beneficial in preventing smooth muscle differentiation and atherosclerosis.

The interaction of α4β1 on inflammatory cells with fibronectin has also been shown to increase chronic allograft failure. Blocking this interaction is beneficial in supporting transplant survival.

The integrin α4β7 (also termed LPAM-1) is expressed on certain sub-populations of T and B lymphocytes and on eosinophils. Like α4β1, α4β7 binds VCAM-1 and fibronectin. In addition α4β7 binds to a cell surface adhesion molecule MAdCAM-1 that is expressed preferentially in the gastrointestinal track and which is believed to be involved in the homing of leukocytes to gastrointestinal mucosa. The interaction between α4β7 and MAdCAM-1 may also be important sites of inflammation outside of mucosal tissue.

Several studies have shown that α4β7 is involved in inflammatory bowel disease and that blocking its function is beneficial.

International patent application WO 00/15612 discloses compounds having a general formula

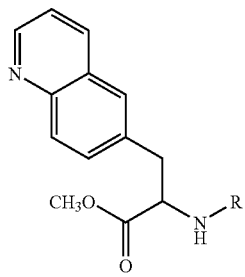

wherein R represents some substituents such as hydrogen, —COOH, —COOalkyl. These compounds can be used as intermediate compounds in a preparation of pharmaceutical compounds, but no pharmaceutical utility for them as such is sought.

International patent application WO 03/093237 discloses 2,6-quinolinyl and 2,6-naphthyl derivatives as pharmaceuticals for the treatment of VLA-4 dependent inflammatory diseases.

We have now found some analogs of these 2,6-quinolinyl compounds that are potent and selective inhibitors of α4 integrins, such as α4β1 and/or α4β7, that demonstrate improved oral bioavailability, a low clearance and a high absorption. These compounds have no or minimal inhibitory action on a integrins of other subgroups.

In one aspect, the invention therefore provides a compound having formula I, its enantiomers, diastereoisomers or a pharmaceutically acceptable salt thereof,

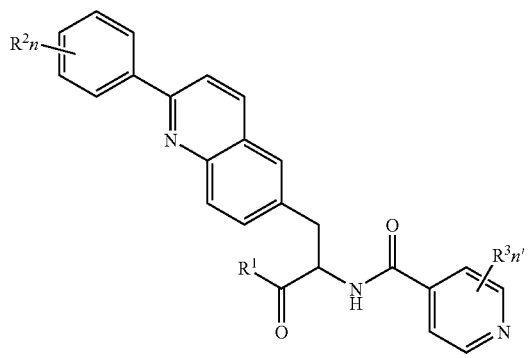

(I)

wherein
$R^1$ is hydrogen, hydroxyl or $C_{1-6}$ alkyl;
$R^2$ is hydrogen or halogen;
n is 0 to 5;
$R^3$ is hydrogen, or halogen;
n' is 0 to 4.

The term "alkyl", as used herein, represents saturated, monovalent hydrocarbon radicals having straight or branched moieties or combinations thereof and containing 1-6 carbon atoms, preferably 1-2 carbon atoms or one of the methylenes (—$CH_2$—) can be replaced by an oxygen atom. Preferred alkyl group is methoxy.

The term "hydroxyl", as used herein, represents a group of formula —OH.

The term "halogen", as used herein, represents chlorine, bromine, fluorine or iodine atom. Preferred halogen is chlorine.

Usually, $R^1$ is hydrogen, hydroxyl or $C_{1-6}$ alkyl. Preferred $R^1$ are hydroxyl and methoxy. Most preferred $R^1$ is hydroxyl.

Usually, $R^2$ is hydrogen or halogen. Preferred $R^2$ is halogen. More preferred $R^2$ is chloride. Most preferred $R^2$ is chloride in positions 2 and 6 of the phenyl ring.

Usually n is 0 to 5. Preferred n is 1, 2 or 3. More preferred n is 2.

Usually, $R^3$ is hydrogen or halogen. Preferred $R^3$ is halogen. More preferred $R^3$ is chloride. Most preferred $R^3$ is chloride in positions 3 and 5 of the pyridine ring.

Usually n' is 0 to 4. Preferred n' is 1, 2 or 3. More preferred n' is 2.

Usually $R^2$ is a chlorine atom in position 2 or 4 of the phenyl ring. Preferably $R^2$ is at least a chlorine atom in position 2 or 4 of the phenyl ring. More preferred $R^2$ is a chlorine atom in position 2 and 4 of the phenyl ring.

Usually $R^3$ is a chlorine atom in position 3 or 5 of the pyridine ring. Preferably $R^3$ is at least a chlorine atom in position 3 or 5 of the pyridine ring. More preferred $R^3$ is a chlorine atom in position 3 and 5 of the pyridine ring.

Preferred compounds are: methyl-(2S)-2-[(3,5-dichloroisonicotinoyl)amino]-3-[2-(2,6-dichlorophenyl)-6-quinolinyl]propanoate and (2S)-2-[(3,5-dichloroisonicotinoyl)amino]-3-[2-(2,6-dichlorophenyl)-6-quinolinyl]propanoic acid and pharmaceutically acceptable salts thereof.

Most preferred compound is (2S)-2-[(3,5-dichloroisonicotinoyl)amino]-3-[2-(2,6-dichlorophenyl)-6-quinolinyl]propanoic acid and pharmaceutically acceptable salts thereof.

Compounds of formula I and some of their intermediates have at least one stereogenic center in their structure. This stereogenic center may be present in a R or a S configuration, said R and S notation is used in correspondence with the rules described in Pure Appl. Chem. (1976), 45, 11-30.

In all the above-mentioned scopes, the asymmetric carbon atom, is preferably in the "S"-configuration.

The "pharmaceutically acceptable salts" according to the invention include therapeutically active, non-toxic base and acid salt forms which the compounds of formula I are able to form.

The acid addition salt form of a compound of formula I that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like (Handbook of Pharmaceutical Salts, P. Heinrich Stahl & Camille G. Wermuth (Eds), Verlag Helvetica Chimica Acta-Zürich, 2002, 329-345).

The compounds of formula I containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like (Handbook of Pharmaceutical Salts, P. Heinrich Stahl & Camille G. Wermuth (Eds), Verlag Helvetica Chimica Acta-Zürich, 2002, 329-345).

Conversely said salt forms can be converted into the free forms by treatment with an appropriate base or acid.

Compounds of formula I and their salts, can be in the form of a solvate, which is included within the scope of the present invention. Such solvates include for example hydrates, alcoholates and the like.

The invention also relates to all stereoisomeric forms such as enantiomeric and diastereoisomeric forms of the compounds of formula I or mixtures thereof (including all possible mixtures of stereoisomers).

Some of the compounds of formula I may also exist in tautomeric forms. Such forms although not explicitly indicated in the above formula are intended to be included within the scope of the present invention.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The present invention concerns also processes for preparing the compounds of formula I.

The compounds of formula I, according to their invention, can be prepared analogously to conventional methods, described in WO 03/093237, as understood by the person skilled in the art of synthetic organic chemistry.

When compounds of formula I present one stereogenic centre, and that non-stereoselective methods of synthesis are used, resolution of the mixture of stereoisomers can best be effected in one or several steps, involving generally sequential separation of mixtures of diastereomers into their constituting racemates, using preferably chromatographic separations on achiral or chiral phase in reversed or preferably in direct mode, followed by at least one ultimate step of resolution of each racemate into its enantiomers, using most preferably chromatographic separation on chiral phase in reversed or preferably in direct mode. Alternatively, when partly stereoselective methods of synthesis are used, the ultimate step may be a separation of diastereomers using preferably chromatographic separations on achiral or chiral phase in reversed or preferably in direct mode.

It has now been found that compounds of formula I and their pharmaceutically acceptable salts are useful in a variety of pharmaceutical indications.

For example, the compounds according to the invention are useful for the treatment of asthma, allergic rhinitis, sinusitis, conjunctivitis, food allergy, inflammatory skin disorders including dermatitis, psoriasis, urticaria, pruritus and eczema, rheumatoid arthritis, inflammatory bowel diseases including Crohn's disease and ulcerative colitis, multiple sclerosis and other autoimmune disorders, acute myelogenous leukaemia, transplantation and atherosclerosis.

Thus, the present invention, in a further aspect, concerns the use of a compound of formula I or a pharmaceutically acceptable salt thereof for the manufacture of a medicament for the treatment of disorders such as mentioned above.

In particular, the present invention concerns the use of a compound of formula I or a pharmaceutically acceptable salt thereof, for the manufacture of a medicament for the treatment of α4β1 and/or α4β7 dependent inflammatory or medical conditions such as for example asthma, allergic rhinitis, sinusitis, conjunctivitis, food allergy, inflammatory skin disorders including dermatitis, psoriasis, urticaria, pruritus and eczema, rheumatoid arthritis, inflammatory bowel diseases including Crohn's disease and ulcerative colitis, multiple sclerosis and other autoimmune disorders, acute myelogenous leukaemia, transplantation and atherosclerosis.

The compounds of the invention are useful for treating conditions mediated by adhesion mechanisms. These conditions include preferably asthma, allergic rhinitis, sinusitis, conjunctivitis, food allergy, inflammatory skin disorders including dermatitis, psoriasis, urticaria, pruritus and eczema, rheumatoid arthritis, inflammatory bowel diseases including Crohn's disease and ulcerative colitis, multiple sclerosis and other autoimmune disorders, acute myelogenous leukaemia, transplantation and atherosclerosis.

Subjects in need of treatment for a α4β1 and/or α4β7 dependent inflammatory or medical condition, preferably asthma, allergic rhinitis, sinusitis, conjunctivitis, food allergy, inflammatory skin disorders including dermatitis, psoriasis, urticaria, pruritus and eczema, rheumatoid arthritis, inflammatory bowel diseases including Crohn's disease and ulcerative colitis, multiple sclerosis and other autoimmune disorders, acute myelogenous leukaemia, transplantation and atherosclerosis, can be treated by administering to the patient an effective amount of one or more of the above-identified compounds or a pharmaceutically acceptable derivative or salt thereof in a pharmaceutically acceptable carrier or diluent to reduce formation of oxygen radicals. The active materials can be administered by any appropriate route, for example, orally, parenterally, intravenously, intradermally, subcutaneously, intramuscularly or topically, in liquid, cream, gel or solid form, via a buccal or nasal spray, or aerosol.

The invention further concerns the use of the compounds of formula I for the manufacture of a medicament for therapeutic application. In particular, the invention concerns the use of the compounds of formula I for the manufacture of a medicament useful for treating conditions in which there is likely to be a $\alpha4\beta1$ and/or $\alpha4\beta7$ dependent component. The invention concerns the use of the compound of formula I for the manufacture of a medicament useful for treating asthma, allergic rhinitis, sinusitis, conjunctivitis, food allergy, inflammatory skin disorders including dermatitis, psoriasis, urticaria, pruritus and eczema, rheumatoid arthritis, inflammatory bowel diseases including Crohn's disease and ulcerative colitis, multiple sclerosis and other autoimmune disorders, acute myelogenous leukaemia, transplantation and atherosclerosis.

The invention further concerns the compounds of formula I for use as medicaments. The invention concerns the compounds of formula I for use as a medicament for treating asthma, allergic rhinitis, sinusitis, conjunctivitis, food allergy, inflammatory skin disorders including dermatitis, psoriasis, urticaria, pruritus and eczema, rheumatoid arthritis, inflammatory bowel diseases including Crohn's disease and ulcerative colitis, multiple sclerosis and other autoimmune disorders, acute myelogenous leukaemia, transplantation and atherosclerosis.

The activity and properties of the active compounds, oral availability and stability in vitro or in vivo can vary significantly among the optical isomers of the disclosed compounds.

In a preferred embodiment, the active compound is administered in an enantiomerically enriched form, i.e., substantially in the form of one isomer.

The present invention also concerns a method for treating $\alpha4\beta1$ and/or $\alpha4\beta7$ dependent inflammatory or medical condition (preferably asthma, allergic rhinitis, sinusitis, conjunctivitis, food allergy, inflammatory skin disorders including dermatitis, psoriasis, urticaria, pruritus and eczema, rheumatoid arthritis, inflammatory bowel diseases including Crohn's disease and ulcerative colitis, multiple sclerosis and other autoimmune disorders, acute myelogenous leukaemia, transplantation and atherosclerosis) in a mammal in need of such treatment, comprising administering a therapeutic dose of at least one compound of formula I or a pharmaceutically acceptable salt thereof to a patient.

The methods of the invention comprise administration to a mammal (preferably human) suffering from above mentioned conditions or disorders, of a compound according to the invention in an amount sufficient to alleviate or prevent the disorder or condition.

The compound is conveniently administered in any suitable unit dosage form, including but not limited to one containing 0.01 to 2000 mg, preferably 0.05 to 500 mg of active ingredient per unit dosage form.

The term "treatment" as used herein includes curative treatment and prophylactic treatment.

The term "substantially" as used herein refers to a composition of or higher than 95% of one isomer, and preferably 98%.

By "curative" is meant efficacy in treating a current symptomatic episode of a disorder or condition.

By "prophylactic" is meant prevention of the occurrence or recurrence of a disorder or condition.

The compounds are of use in modulating cell adhesion and in particular are of use in the prophylaxis and treatment of diseases or disorders in which the extravasation of leukocytes plays a role and the invention extends to such a use and to the use of the compounds for the manufacture of a medicament for treating such diseases or disorders, Diseases or disorders of this type include inflammatory arthritis such as rheumatoid arthritis, vasculitis or polydermatomyositis, multiple sclerosis, transplantation, diabetes, inflammatory dermatoses such as psoriasis or dermatitis, asthma and inflammatory bowel disease.

One aspect of the invention includes methods for treating $\alpha4$-related cancers (including cancers, whether solid or haematopoietic). Examples of such cancers include, but are not limited to, lung e.g. non-small cell lung, pancreatic, prostate, renal, cervical, ovarian, colorectal, mammary carcinoma, endometrial, bladder, malignant melanoma, seminomas, thyroid, acute myelogenous leukaemia and gastric cancer.

Results obtained with compounds of formula I are indicative of a strong pharmacological effect.

For treating diseases, compounds of formula I or their pharmaceutically acceptable salts, may be employed at an effective daily dosage and administered in the form of a pharmaceutical composition.

Therefore, another embodiment of the present invention concerns a pharmaceutical composition comprising an effective amount of a compound of formula I or a pharmaceutically acceptable salt thereof in combination with a pharmaceutically acceptable diluent or carrier.

To prepare a pharmaceutical composition according to the invention, one or more of the compounds of formula I or a pharmaceutically acceptable salt thereof, is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, or parenteral.

Pharmaceutical compositions comprising compounds according to the invention can, for example, be administered orally or parenterally, i.e., intravenously, intramuscularly, subcutaneously or intrathecally.

Pharmaceutical compositions suitable for oral administration can be solids or liquids and can, for example, be in the form of tablets, pills, dragees, gelatine capsules, solutions, syrups, and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula I in compositions for oral administration is at least 0.5% by weight and can be up to 80% by weight with respect to the total weight of the composition.

For the preferred oral compositions, the daily dosage is in the range 0.01 to 2000 milligrams (mg) of compounds of formula I.

In compositions for parenteral administration, the quantity of compound of formula I present is at least 0.5% by weight and can be up to 33% by weight with respect to the total weight of the composition. For the preferred parenteral compositions, the dosage unit is in the range 0.01 mg to 2000 mg of compounds of formula I.

The daily dose can fall within a wide range of dosage units of compound of formula I and is generally in the range 0.01 to 2000 mg. However, it should be understood that the specific doses could be adapted to particular cases depending on the individual requirements, at the physician's discretion.

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

The IUPAC names of the compounds mentioned in the examples were generated with ACD version 6.00.

Unless specified otherwise in the examples, characterization of the compounds is performed according to the following methods:

NMR spectra are recorded on a Bruker AV-300 or DRX-400 Spectrometers operating at 300.13 MHz or 400.13 MHz for protons, and running the Bruker XWINNMR software package. Spectra were acquired at room temperature unless otherwise stated. Chemical shifts are given in ppm referenced either to internal TMS or to the residual solvent signal.

HPLC analyses are performed using one of the following system: an HP 1100 (Diode Array) linked to a Finnigan LC-Q Mass Spectrometer, ESI mode with Pos/Neg ionisation, Detector Wavelength DAD 200-400 nm, mounted with a LUNA C18(2), DP 5 μm, 100×4.6 mm analytical column. The gradient ran from solvent A (water+0.08% formic acid) to solvent B (acetonitrile+0.08% formic acid) in 6.5 min with a hold at 95% B of 9.7 min and at 5% B of 11.82 min. The flow rate is set at 3 ml/min. The chromatography is carried out at 35° C.

The following abbreviations are used in the examples:

| | |
|---|---|
| TFA | Trifluoroacetic acid |
| TEA | Triethylamine |
| DCM | Dichloromethane |
| NaOH | Sodium hydroxide |
| HCl | Hydrochloric acid |
| NaHCO3 | Sodium hydrogencarbonate |
| MgSO4 | Magnesium sulphate |
| THF | Tetrahydrofuran |
| MgCl H2O | Magnesium chloride monohydrate |
| NaCl | Sodium chloride |
| H2O2 | Hydrogen peroxide |
| MeOH | Methanol |
| EtOH | Ethanol |
| EtAc | Ethyl acetate |
| CaCl2 | Calcium chloride |
| KCl | Potassium chloride |
| MnCl2 | Manganese chloride |
| NaH2PO4 2H2O | Sodium phosphate monobasic dihydrate |
| TMB | Tetramethyl benzidine |
| PBS | Phosphate buffered saline |
| TBS | Tris buffered saline |
| ADP | Adenosine 5'-diphosphate |
| BSA | Bovine serum albumin |
| FCS | Foetal calf serum |
| Room temperature | RT |
| W | weight |
| V | volume |

EXAMPLE 1

Synthesis of methyl-(2S)-2-[(3,5-dichloroisonicotinoyl)amino]-3-[2-(2,6-dichlorophenyl)-6-quinolinyl]propanoate. (1)

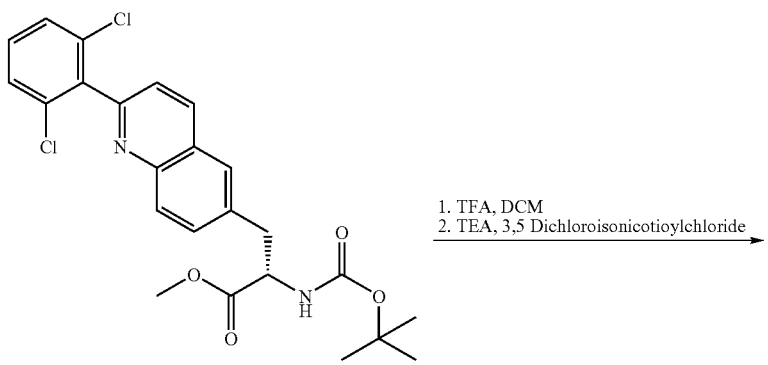

1. TFA, DCM
2. TEA, 3,5 Dichloroisonicotioylchloride

No 26, UCB Patent WO03093237

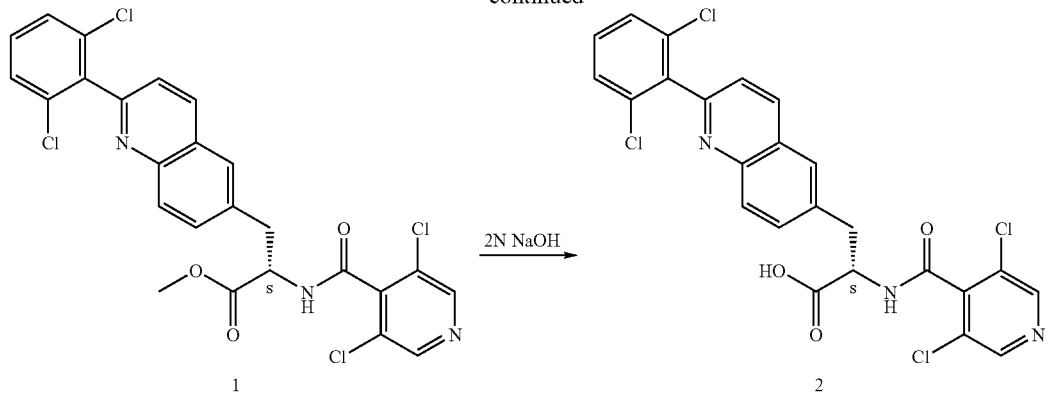

Methyl-(2S)-2-[(tert-butoxycarbonyl)amino]-3-[2-(2,6-dichlorophenyl)-6-quinolinyl]propanoate (compound No 26, international patent application WO 03/093237) (500 mg, 1.05 mmol) was dissolved in DCM (5 ml) and a solution of TFA (0.8 ml, 10.5 mmol) in DCM (2 ml) was added drop wise over 10 minutes. After addition was complete the reaction was stirred at RT over night. The reaction was cooled to 0° C. and TEA (2.1 ml, 15.8 mmol) in DCM (2 ml) was added drop wise over 10 minutes. The reaction was cooled to −10° C. and 3,5 dichloro-isonicotinoylchloride (*Bioorg. Med. Chem. Lett.* 2002, 12, 1591-1594), (663 mg, 3.0 mmol) was added drop wise over 10 minutes, before allowing the reaction to warm to RT. After 1 hour the reaction was washed with aqueous HCl (1N, 10 ml), followed by washing with aqueous NaHCO3 solution (saturated, 10 ml). The DCM layer was dried over MgSO4, filtered and the solvent removed in vacuo to yield an off white solid. The solid was purified using flash chromatography (eluent EtAc) to yield the title compound as a white powder (432 mg, 75%) LCMS M+1 (552, 550, 548), Retention Time 3.82 min, $^1$H NMR, 300 Mz, $d_6$-DMSO-9.50 (1H, d), 8.63 (2H, s), 8.42 (1H, d), 7.98 (1H, d), 7.94 (1H, d), 7.78 (1H, dd), 7.65 (2H, d), 7.55 (2H, m), 4.95 (1H, m), 3.74 (3H, s), 3.45 (1H, dd), 3.20 (1H, dd).

EXAMPLE 2

Synthesis of (2S)-2-[(3,5-dichloroisonicotinoyl)amino]-3-[2-(2,6-dichlorophenyl)-6-quinolinyl]propanoic acid. (2)

Methyl-(2S)-2-[(3,5-dichloroisonicotinoyl)amino]-3-[2-(2,6-dichlorophenyl)-6-quinolinyl]propanoate (410 mg, 0.75 mmol) was dissolved in THF (2 ml) and added drop wise over 3 hrs to a stirred aqueous solution of NaOH (2 M, 2.5 ml). After addition was complete the reaction was stirred at RT for 1 hour, before the THF was removed in vacuo. The resulting slurry was diluted with water (6 ml) and acidified to pH-4 using HCl (12 M). The resultant precipitate was collected by filtration, washed with water (15 ml) and dried overnight in vacuo (40° C.) to yield the desired product as a white powder (274 mg, 68%). LCMS M+1 (535, 537), M−1 (534, 536) Retention Time 3.39 min, $^1$H NMR, 300 Mz, $d_6$-DMSO-13.00 (1H, brs), 9.40 (1H, d), 8.65 (2H, s), 8.42 (1H, d), 7.98 (1H, d), 7.94 (1H, d), 7.78 (1H, dd), 7.65 (2H, d), 7.54 (2H, m), 4.90 (1H, m), 3.45 (1H, brs), 3.20 (1H, dd). Chiral HPLC 97% ee Retention time 6.29 min (Column-CHIRALPAK AD 250*4.6 mm, 10 m; Solvent A 1-Propanol+0.1% TFA, Solvent B Isohexane; Isocratic 20% A: 80% B; Temperature 40° C.; Run Time 15 min; Detection 280 nM).

EXAMPLE 3

The following cellular assays are used to demonstrate the potency and selectivity of the compounds according to the invention. In each of these assays an $IC_{50}$ value was determined for each test compound and represents the concentration of compound necessary to achieve 50% inhibition of cell adhesion where 100%=adhesion assessed in the absence of the test compound and 0%=absorbance in wells that did not receive cells.

α4β1 Integrin-Dependent Jurkat Cell Adhesion to VCAM-Ig:

96 well NUNC plates were coated with F(ab)$_2$ fragment goat anti-human IgG Fcγ-specific antibody [Jackson Immuno Research 109-006-098: 100 μl at 2 μg/ml in 0.1M NaHCO$_3$, pH 8.4], overnight at 4° C. The plates were washed (3×) in PBS and then blocked for 1 h in PBS/1% BSA at RT on a rocking platform. After washing (3× in PBS) 9 ng/ml of purified 2d VCAM-Ig diluted in PBS/1% BSA was added and the plates left for 60 minutes at RT on a rocking platform. The plates were washed (3× in PBS) and the assay then performed at 37° C. for 30 min in a total volume of 200 μl containing 2.5×10$^5$ Jurkat cells in the presence or absence of titrated test compounds.

Each plate was washed (2×) with medium and the adherent cells were fixed with 100 μl MeOH for 10 minutes followed by another wash. 100 μl 0.25% Rose Bengal (Sigma R4507) in PBS was added for 5 minutes at RT and the plates washed (3×) in PBS. 100 μl 50% (v/v) EtOH in PBS was added and the plates left for 60 min after which the absorbance (570 nm) was measured.

α4β7 Integrin-Dependent JY Cell Adhesion to MAdCAM-Ig:

This assay was performed in the same manner as the α4β1 assay except that MAdCAM-Ig (150 ng/ml) was used in place of 2d VCAM-Ig and a sub-line of the β-lymphoblastoid cell-line JY was used in place of Jurkat cells. The $IC_{50}$ value for each test compound was determined as described in the α4β1 integrin assay.

Whole Blood VCAM-Binding Assay for α4 Integrins:

The following reagents were added to FACS tubes: 3 μl 100 mM MnCl$_2$ (100× required conc), 1 μl 1 mg/ml streptavidin-FITC (supplier Pierce 100× required conc), 2 μl 500 μg/ml biotinylated hVCAM-1-mFc (50× required conc), and 2 μl serially-diluted test compound at 50× desired final concentrations. 100 μl heparinised blood from healthy human donors was then added to each FACS tube which were then sealed and rocked for 30 minutes at RT. 2 ml "FACS Lysing Solution" (BD Biosciences) solution was added to tubes for 5 minutes at room temperature RT, and tubes were spun at 1200 rpm and washed 2× in 3 ml TBS, before final suspension in 100 μl TBS. Flow cytometry was then performed on a Becton Dickinson FACScan to assess the % of cells in the lymphocyte gate capable of binding VCAM.

α5β1 Integrin-Dependent K562 Cell Adhesion to Fibronectin:

96 well tissue culture plates were coated with human plasma fibronectin (Sigma F0895) at 5 g/ml in PBS for 2 hr at 37° C. The plates were washed (3× in PBS) and then blocked for 1 h in 100 l PBS/1% BSA at RT on a rocking platform. The blocked plates were washed (3× in PBS) and the assay then performed at 37° C. in a total volume of 200 μl containing $2.5 \times 10^5$ K562 cells, phorbol-12-myristate-13-acetate at 10 ng/ml, and in the presence or absence of titrated test compounds. Incubation time was 30 minutes. Each plate was fixed and stained as described in the α4β1 assay above.

αmβ2-Dependent Human Polymorphonuclear Neutrophils Adhesion to Plastic:

96 well tissue culture plates were coated with RPMI 1640/10% FCS for 2 h at 370° C. $2 \times 10^5$ freshly isolated human venous polymorphonuclear neutrophils (PMN) were added to the wells in a total volume of 200 l in the presence of 10 ng/ml phorbol-12-myristate-13-acetate, and in the presence or absence of test compounds, and incubated for 20 min at 37° C. followed by 30 min at room temperature RT. The plates were washed in medium and 100 μl 0.1% (w/v) hexadecyl trimethyl ammonium bromide (Sigma H5882) in 0.05 M potassium phosphate buffer, pH 6.0 added to each well. The plates were then left on a rocker at room temperature RT for 60 min. Endogenous peroxidase activity was then assessed using TMB as follows: PMN lysate samples mixed with 0.22% $H_2O_2$ (Sigma) and 50 μg/ml TMB (Boehringer Mannheim) in 0.1M sodium acetate/citrate buffer, pH 6.0 and absorbance measured at 630 nm.

αIIb/β3-Dependent Human Platelet Aggregation:

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of $6 \times 10^8$/ml in autologous plasma. Cuvettes contained equal volumes of PRP and filtered Tyrode's buffer (g/liter: NaCl 8.0; $MgCl_2.H_2O$ 0.427; $CaCl_2$ 0.2; KCl 0.2; D-glucose 1.0; $NaHCO_3$ 1.0; $NaH2PO_4.2H_2O$ 0.065). Aggregation was monitored following addition of 2.5 M ADP (Sigma) in the presence or absence of inhibitors.

αvβ3 Integrin-Dependent JY Adhesion to Vitronectin:

96 well NUNC plates are coated with human vitronectin (Promega) at 2.5 g/ml in PBS for 2 hours at 370° C. The plates were washed (2× in PBS) and then blocked for 1 h in 100 l PBS/1% BSA at RT on a rocking platform. The blocked plates were then washed (2× in PBS) and the assay was then performed at 370° C. in a total volume of 200 μl containing $2 \times 10^5$ JY cells, phorbol-12-myristate-13-acetate at 10 ng/ml, and in the absence or presence of titrated test compound. The JY cells were preincubated for 15 minutes with 5 μg/ml monoclonal antibody against β2 integrins, called 6.5E, to prevent β2-dependent non-specific binding. Each plate was fixed and stained as described above in the α4β1 assay above.

In the above assays compounds of the invention such as the compounds of the examples generally have $IC_{50}$ values in the α4β1 assay of 1 μM and below and in the α4β7 assay of 1 μM and below. In the other assays featuring a integrins of other subgroups the same compounds had $IC_{50}$ values of > 50 μM and above thus demonstrating the potency and selectivity of their action against α4 integrins.

The invention claimed is:

1. Compound having formula I, including its enantiomers and diastereoisomers, in free or pharmaceutically acceptable salt form,

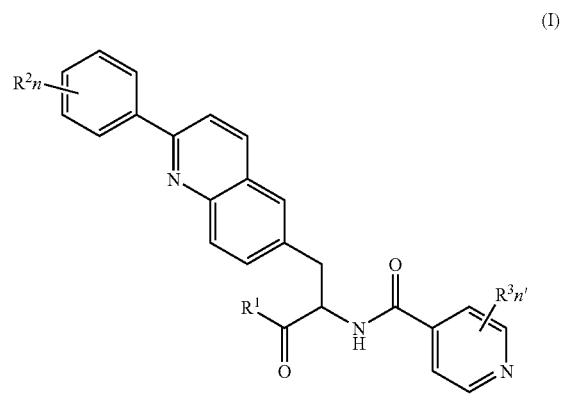

(I)

wherein
$R^1$ is hydrogen, hydroxyl or $C_{1-6}$ alkyl;
$R^2$ is hydrogen or halogen;
n is 0 to 5;
$R^3$ is hydrogen, or halogen;
n' is 0 to 4.

2. A compound according to claim 1, wherein
$R^1$ is hydroxyl or methoxy;
$R^2$ is chloride;
n is 2;
$R^3$ is chloride
n' is 2.

3. A compound according to claim 1, wherein the asymmetric carbon atom is in the "S"-configuration.

4. A compound according to claim 1 selected from methyl-(2S)-2-[(3,5-dichloroisonicotinoyl)amino]-3-[2-(2,6-dichlorophenyl)-6-quinolinyl]propanoate and (2S)-2-[(3,5-dichloroisonicotinoyl)amino]-3-[2-(2,6-dichlorophenyl)-6-quinolinyl]propanoic acid, in free or pharmaceutically acceptable salt form.

5. Compound (2S)-2-[(3,5-dichloroisonicotinoyl)amino]-3-[2-(2,6-dichlorophenyl)-6-quinolinyl]propanoic acid, in free or pharmaceutically acceptable salt form.

6. A pharmaceutical composition comprising as active ingredient a therapeutically effective amount of a compound according to claim 1 and a pharmaceutically acceptable adjuvant, diluent or carrier.

7. A pharmaceutical composition according to claim 6 wherein the compound is selected from methyl-(2S)-2-[(3,5-dichloroisonicotinoyl)amino]-3-[2-(2,6-dichlorophenyl)-6-quinolinyl]propanoate and (2S)-2-[(3,5-dichloroisonicotinoyl)amino]-3-[2-(2,6-dichlorophenyl)-6-quinolinyl] propanoic acid, and wherein the compound is in free or pharmaceutically acceptable salt form.

8. A pharmaceutical composition according to claim 7 wherein the compound is (2S)-2-[(3,5-dichloroisonicotinoyl)amino]-3-[2-(2,6-dichlorophenyl)-6-quinolinyl]propanoic acid, in free or pharmaceutically acceptable salt form.

* * * * *